United States Patent
Li et al.

(10) Patent No.: US 11,040,213 B2
(45) Date of Patent: Jun. 22, 2021

(54) METHODS AND IMPLANTABLE MEDICAL DEVICES FOR DETECTING A MAGNETIC FIELD

(71) Applicant: PACESETTER, INC., Sylmar, CA (US)

(72) Inventors: Anthony J. Li, Valencia, CA (US); Xing Pei, Thousand Oaks, CA (US)

(73) Assignee: PACESETTER, INC., Sylmar, CA (US)

( * ) Notice: Subject to any disclaimer, the term of this patent is extended or adjusted under 35 U.S.C. 154(b) by 352 days.

(21) Appl. No.: 15/913,770

(22) Filed: Mar. 6, 2018

(65) Prior Publication Data

US 2019/0275343 A1    Sep. 12, 2019

(51) Int. Cl.
| | | |
|---|---|---|
| *A61N 1/37* | (2006.01) | |
| *A61N 1/372* | (2006.01) | |
| *A61N 1/39* | (2006.01) | |
| *A61N 1/08* | (2006.01) | |
| *A61B 5/00* | (2006.01) | |

(52) U.S. Cl.
CPC ..... *A61N 1/37252* (2013.01); *A61N 1/37223* (2013.01); *A61B 5/0031* (2013.01); *A61N 1/08* (2013.01); *A61N 1/3925* (2013.01); *A61N 1/3956* (2013.01)

(58) Field of Classification Search
CPC .......... A61B 5/0031; A61N 1/08; A61N 1/37; A61N 1/3706; A61N 1/37223; A61N 1/37252; A61N 1/3925; A61N 1/3956
See application file for complete search history.

(56) References Cited

U.S. PATENT DOCUMENTS

| | | | |
|---|---|---|---|
| 8,014,867 B2 * | 9/2011 | Cooke ................. | A61N 1/3718 607/31 |
| 8,391,980 B2 | 3/2013 | Bornzin et al. | |
| 9,044,610 B2 | 6/2015 | Rosenberg et al. | |
| 9,216,285 B1 | 12/2015 | Boling et al. | |
| 9,232,485 B2 | 1/2016 | Wu et al. | |
| 9,333,351 B2 | 5/2016 | Arnold et al. | |
| 2006/0293591 A1 * | 12/2006 | Wahlstrand ......... | A61N 1/3706 600/423 |
| 2009/0157146 A1 * | 6/2009 | Linder ............... | A61N 1/37217 607/60 |
| 2013/0096551 A1 | 4/2013 | Ozawa et al. | |

* cited by examiner

*Primary Examiner* — Amanda K Hulbert
(74) *Attorney, Agent, or Firm* — The Small Patent Law Group LLC; Dean D. Small

(57) ABSTRACT

Methods and devices are provided for detecting a magnetic field in a presence of an implantable medical device (IMD). The IMD includes at least one electrode and a magnetic detection sensor configured to detect a magnetic field of an external magnetic source. The IMD includes a notification circuit, and an arrhythmia circuit configured to analyze cardiac signals sensed by the electrode and to deliver a therapy based on the cardiac signals. The IMD includes an electronics circuit that is configured to suspend the delivery of the therapy in response to detection of the magnetic field by the magnetic field sensor. The electronics circuit is configured to trigger the notification circuit to generate a notification output in response to the detection of the magnetic field indicating that the therapy has been suspended.

12 Claims, 8 Drawing Sheets

METHODS AND IMPLANTABLE MEDICAL DEVICES FOR DETECTING A MAGNETIC FIELD

BACKGROUND

Embodiments of the present disclosure generally relate to methods and implantable medical devices for detecting a magnetic field.

Today magnets are utilized in connection with implantable medical devices (IMDs). For example, a magnet may be used to direct an IMD to suspend tachycardia detection and prevent delivery of tachyarrhythmia therapy. However, conventional devices experience limits in that improper placement of the magnet does not prevent the delivery of tachycardia therapy. The improper placement of the magnet allows for continuous delivery of high-voltage therapies to patients with IMDs. Conventional devices provide little or no feedback concerning detection of a magnetic field by the device.

SUMMARY

In accordance with embodiments herein, an implantable medical device (IMD) is provided. The implantable medical device includes at least one electrode, and a magnetic detection sensor configured to detect a magnetic field of an external magnetic source. The device includes a notification circuit, and an electronics circuit configured to analyze cardiac signals sensed by the electrode and to deliver a therapy based on the cardiac signals. The electronics circuit is configured to suspend the delivery of the therapy in response to detection of the magnetic field by the magnetic field sensor. The electronics circuit is further configured to trigger the notification circuit to generate a notification output in response to the detection of the magnetic field indicating that the therapy has been suspended.

Optionally, the magnetic detection sensor may be configured to provide a magnetic field present (MFP) signal to the electronics circuit when the magnetic field sensor experiences a magnetic field that has a strength that exceeds a stable field duration. The electronics circuit may be configured to trigger the notification circuit to generate a field detected indicator, as the notification, when the MFP signal is maintained for a period of time that exceeds a stable field duration. The electronics circuit may be configured to direct the notification circuit to generate a field loss indicator when the magnetic field sensor indicated that the magnetic field has terminated. The notification circuit may be configured to provide at least one of an auditory or vibratory notification indicating that a magnetic field is present and has a strength that exceeds a field strength threshold.

The notification may represent a stimulus with first and second unique patterns that differentiate between activation and de-activation of the magnetic field. The electronics circuit may include a microcontroller and the magnetic detection sensor sets a status register of the microcontroller, the microcontroller configured to confirm a magnet placement when the status register is set for a stable field duration. The electronics circuit may be configured delivery a tachyarrhythmia therapy and to suspend the delivery of the tachyarrhythmia therapy in response to detection of the magnetic field by the magnetic field sensor. The magnetic field sensor may include at least one of a Hall Effect sensor, a giant magnetoresistance sensor, or a reed switch.

In accordance with embodiments herein, a method is provided. To manage an implantable medical device (IMD) that includes at least one electrode and an electronics circuit configured to analyze cardiac signals sensed by the electrode and to deliver a therapy based on the cardiac signals. The method includes detecting, at a magnetic detection sensor, a magnetic field of an external magnetic source. The method includes suspending the delivery of the therapy in response to detection of the magnetic field. The method includes generating a notification output, in response to the detection of the magnetic field, indicating that the therapy has been suspended.

Responsive to placing a magnet over a region of a patient proximate to an implant location of the IMD, the magnet producing a magnetic field that includes multiple null zones, the detecting operation including detecting whether the IMD is located at least partially in one of the null zones. The method may determine whether the magnetic field sensor experiences a magnetic field having a strength that exceeds a stable field duration and providing a magnetic field present (MFP) signal to the electronics circuit based on the determining. The method may identify when the MFP signal is maintained for a period of time that exceeds a stable field duration and generating a field detected indicator, as the notification based on the identifying. The method may generate a field loss indicator when the magnetic field sensor indicated that the magnetic field has reduced to below the detection threshold (e.g., including a hysteresis) indicate a magnet is removed. The generating comprises providing at least one of an auditory or vibratory notification indicating that a magnetic field is present and has a strength that exceeds a field strength threshold.

The notification may represent a stimulus with first and second unique patterns that differentiate between activation and de-activation of the suspension of the therapy. The magnetic detection sensor may include a microcontroller and the method sets a status register of the microcontroller, the microcontroller configured to confirm a magnet placement when the status register is set for a stable field duration. The electronics circuit may be configured delivery a tachyarrhythmia therapy and to suspend the delivery of the tachyarrhythmia therapy in response to detection of the magnetic field by the magnetic field sensor. The magnetic field sensor may include at least one of a Hall Effect sensor, a giant magnetoresistance sensor, or a reed switch. The method may deliver a tachyarrhythmia therapy when a magnet is placed over a region of a patient proximate to an implant location of the IMD such that the IMD is located in a null zone of the magnet.

DETAILED DESCRIPTION

Figure 1:
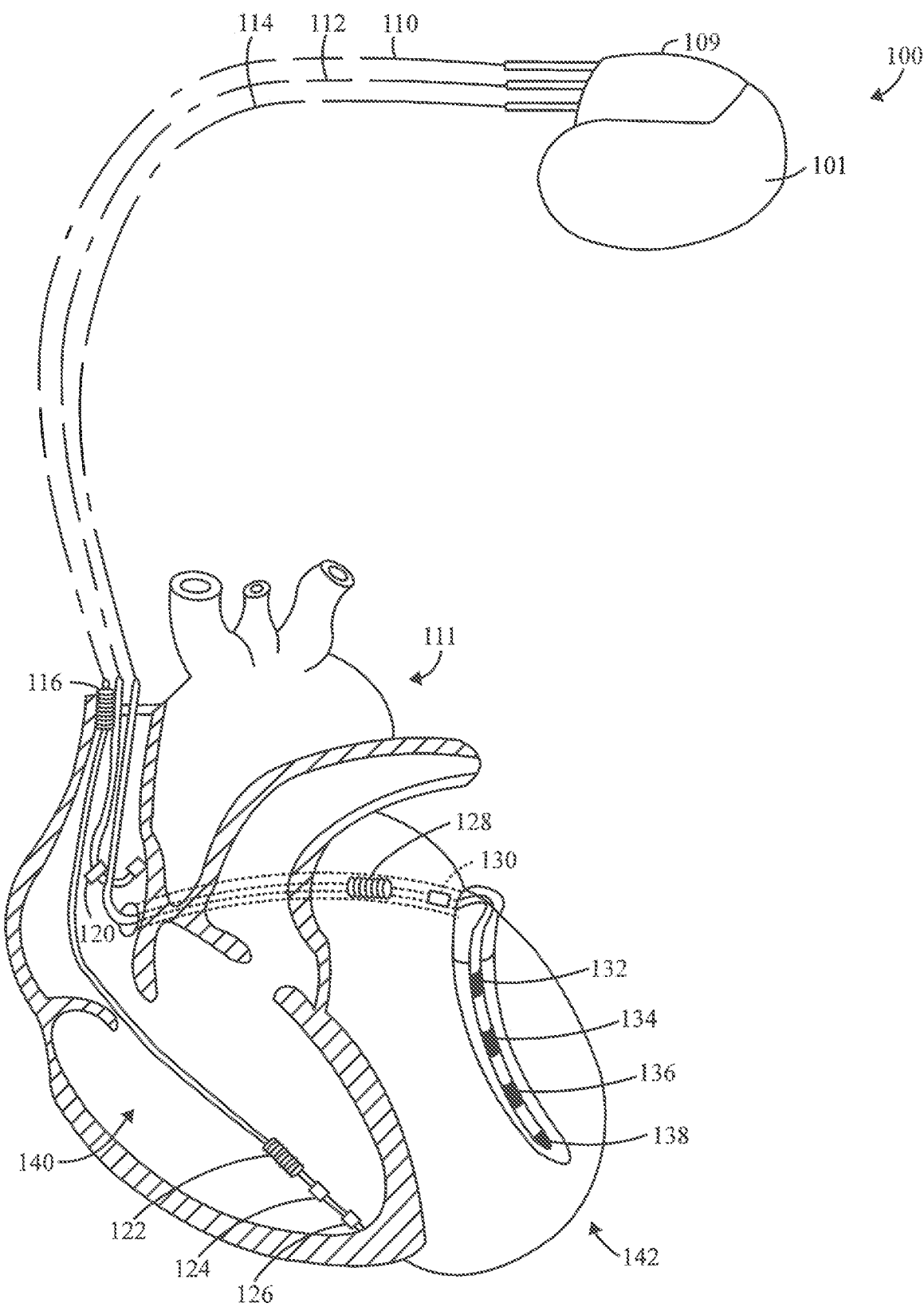
FIG. 1 illustrates a schematic view of an implantable medical device, in accordance with an embodiment.

It will be readily understood that the components of the embodiments as generally described and illustrated in the Figures herein, may be arranged and designed in a wide variety of different configurations in addition to the described example embodiments. Thus, the following more detailed description of the example embodiments, as represented in the Figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etc. In other instances, well-known structures, materials, or operations are not shown or described in detail to avoid obfuscation. The following description is intended only by way of example and simply illustrates certain example embodiments.

The systems and methods described herein may employ structures or aspects of various embodiments discussed herein. In various embodiments, certain operations may be omitted or added, certain operations may be combined, certain operations may be performed simultaneously, certain operations may be performed concurrently, certain operations may be split into multiple operations, certain operations may be performed in a different order, or certain operations or series of operations may be re-performed in an iterative fashion. It should be noted that other methods may be used, in accordance with an embodiment herein. Further, wherein indicated, the methods may be fully or partially implemented by one or more processors of one or more devices or systems. While the operations of some methods may be described as performed by the processor(s) of one device, additionally, some or all of such operations may be performed by the processor(s) of another device described herein.

Conventional methods do not provide any feedback mechanisms to indicate when a magnet is detected and the therapy is suspended by the implantable medical device (IMD), unless it is interrogated by a programmer. All magnets include a plurality of null zones where the magnetic field is low (e.g., below 10 Gauss). For example, when the toroidal magnet and the IMD are spaced 3 cm apart, at least some magnets exhibit a null zone (e.g., no magnetic field) that encompasses a 2 cm area along a center axis of the magnet. When the same magnet is spaced a 5 cm distance between the magnet and the IMI, the magnet will exhibit a null zone that encompasses a 4 cm area along the center axis of the magnet. When the IMI is positioned within the null zone of the magnetic field, the IMD does not perform the expected function, such as suspending tachyarrhythmia therapy.

Embodiments may be implemented in connection with one or more implantable medical devices (IMDs). Non-limiting examples of IMDs include one or more of neurostimulator devices, implantable leadless monitoring and/or therapy devices, and/or alternative implantable medical devices. For example, the IMD may represent a cardiac monitoring device, pacemaker, cardioverter, cardiac rhythm management device, defibrillator, neurostimulator, leadless monitoring device, leadless pacemaker, and/or the like. For example, the IMD may include one or more structured and/or functional aspects of the device(s) described in U.S. Pat. No. 9,333,351 "Neurostimulation Method And System To Treat Apnea" and U.S. Pat. No. 9,044,610 "System And Methods For Providing A Distributed Virtual Stimulation Cathode For Use With An Implantable Neurostimulation System", which are hereby incorporated by reference. Additionally or alternatively, the IMD may include one or more structural and/or functional aspects of the device(s) described in U.S. Pat. No. 9,216,285 "Leadless Implantable Medical Device Having Removable And Fixed Components" and U.S. Pat. No. 8,831,747 "Leadless Neurostimulation Device And Method Including The Same", which are hereby incorporated by reference. Additionally or alternatively, the IMD may include one or more structural and/or functional aspects of the device(s) described in U.S. Pat. No. 8,391,980 "Method And System For Identifying A Potential Lead Failure In An Implantable Medical Device" and U.S. Pat. No. 9,232,485 "System And Method For Selectively Communicating With An Implantable Medical Device", which are hereby incorporated by reference.

In accordance with an embodiment, methods and devices are provided that indicate, to the user (e.g., physician, patient), detection of a magnetic field by the IMD. Responsive to the detection of a magnetic field, the embodiment triggers the activation of an auditory alert and/or vibrator alert to inform the physician and/or patient that the IMD detects the magnetic field. For example, a notification may deliver non-therapeutic stimulus in unique patterns that differentiate between the activation and/or detection of the magnetic field relative to an activation and/or termination of the magnetic field.

FIG. 1 illustrates an implantable medical device (IMD) 100 in electrical communication with multiple leads implanted into a patient's heart 111. The IMD 100 may be a dual-chamber stimulation device, capable of treating both fast and slow arrhythmias with stimulation therapy, including cardioversion, pacing stimulation, an implantable cardioverter defibrillator, suspend tachycardia detection, tachyarrhythmia therapy, and/or the like.

The IMD 100 includes a housing 101 to hold the electronic/computing components. The housing 101 (which is often referred to as the "can", "case", "encasing", or "case electrode") may be programmably selected to act as the return electrode for certain stimulus modes. The housing 101 further includes a connector 109 with a plurality of terminals 102, 105, 106, 107, 108.

The IMD 100 is shown in electrical connection with a heart 111 by way of a left atrial (LA) lead 120 having a right lead 112 and a left atrial (LA) ring electrode 128. The IMD 100 is also in electrical connection with the heart 111 by way of a right ventricular (RV) lead 110 having, in this embodiment, a left ventricle (LV) electrode 132, an LV ring electrode 134, an LV electrode 136, and an LV electrode 138. The RV lead 110 is transvenously inserted into the heart 111 to place the RV coil 122 in the RV apex, and the SVC coil electrode 116. Accordingly, the RV lead 110 is capable of receiving cardiac signals and delivering stimulation in the form of pacing and shock therapy to the right ventricle 140 (also referred to as the RV chamber).

The IMD 100 includes a left ventricle 142 (e.g., left chamber) pacing therapy, and is coupled to a multi-pole LV lead 114 designed for placement in various locations such as a "CS region" (e.g., venous vasculature of the left ventricle, including any portion of the coronary sinus (CS), great cardiac vein, left marginal vein, left posterior ventricular vein, middle cardiac vein, and/or small cardiac vein or any other cardiac vein accessible by the coronary sinus), the epicardial space, and/or the like. In an embodiment, the LV lead 114 is designed to receive atrial and ventricular cardiac signals and to deliver left ventricular pacing therapy using a set of multiple LV electrodes 132, 134, 136, 138. The LV lead 114 also may deliver left atrial pacing therapy using at least an LA ring electrode 128 and shocking therapy using at least the LA ring electrode 128. In alternate embodiments, the LV lead 114 includes the LV electrodes 138, 136, 134, and 132, but does not include the LA electrode 130. The LV lead 114 may be, for example, the Quartet™ LV pacing lead developed by St. Jude Medical Inc. (headquartered in St. Paul, Minn.), which includes four pacing electrodes on the LV lead. Although three leads 110, 112, and 114 are shown in FIG. 1, fewer or additional leads with various configurations of pacing, sensing, and/or shocking electrodes may optionally be used. For example, the LV lead 114 may have more or less than four LV electrodes 132-138.

When selecting a target venous branch for the LV lead 114, several factors may be taken into account. For example, it may be desirable to maximize the LV mass that may be captured by the LV lead 114. Accordingly, to maximize LV mass exposure, certain venous branches may be preferred for positioning the LV lead 114. Further, a diameter and trajectory of the venous branch are also considered to ensure that the venous branch will support chronic stability of the LV lead 114. Passive fixation of the LV lead 114 may be established through the anatomy of the host venous branch which causes the LV lead 114 to extend the distal portion thereof in a manner that differs from the LV lead's preformed shape. Optionally, additional factors to be considered when placing the LV lead 114 may include reducing myocardial capture thresholds, avoiding atrial and phrenic nerve stimulation and the like. After the LV lead 114 is positioned, the LV pacing vectors may be selected.

The LV electrode 138 (also referred to as P4) is shown as being the most "distal" LV electrode with reference to how far the electrode is from the right ventricle 140. The LV electrode 132 (also referred to as D1) is shown as being the most "proximal" LV electrode 132-138 to the left ventricle 142. The LV electrodes 136 and 134 are shown as being "middle" LV electrodes (also referred to as M3 and M2), between the distal and proximal LV electrodes 138 and 132, respectively. Accordingly, so as to more aptly describe their relative locations, the LV electrodes 138, 136, 134, and 132 may be referred to respectively as electrodes D1, M2, M3, and P4 (where "D" stands for "distal", "M" stands for "middle", and "P" stands from "proximal", and the s are arranged from most distal to most proximal, as shown in FIG. 1). Optionally, more or fewer LV electrodes may be provided on the lead 114 than the four LV electrodes D1, M2, M3, and P4.

The LV electrodes 132-138 are configured such that each electrode may be utilized to deliver pacing pulses and/or sense pacing pulses (e.g., monitor the response of the LV tissue to a pacing pulse). In a pacing vector or a sensing vector, each LV electrode 132-138 may be controlled to function as a cathode (negative electrode). Pacing pulses may be directionally provided between electrodes to define a pacing vector. In a pacing vector, a generated pulse is applied to the surrounding myocardial tissue through the cathode. The electrodes that define the pacing vectors may be electrodes in the heart 111 or located externally to the heart 111 (e.g., on a housing/case device 101). For example, the housing/case 101 may be referred to as the housing 101 and function as an anode in unipolar pacing and/or sensing vectors. The RV coil 122 may also function as an anode in unipolar pacing and/or sensing vectors. The LV electrodes 132-138 may be used to provide various different vectors. Some of the vectors are intraventricular LV vectors (e.g., vectors between two of the LV electrodes 132-138), while other vectors are interventricular vectors (e.g., vectors between an LV electrode 132-138 and the RV coil 122 or another electrode remote from the left ventricle 142). Below is a list of exemplary bipolar sensing vectors with LV cathodes that may be used for sensing using the LV electrodes D1, M2, M3, and P4 and the RV coil 122. It is recognized that various other types of leads and IMDs may be used with various other types of electrodes and combinations of electrodes. The foregoing electrode types/combinations are provided as non-limiting examples. Further, it is recognized that utilizing an RV coil electrode as an anode is merely one example, Various other electrodes may be configured as the anode electrode.

Implantable Medical Device

Figure 2:
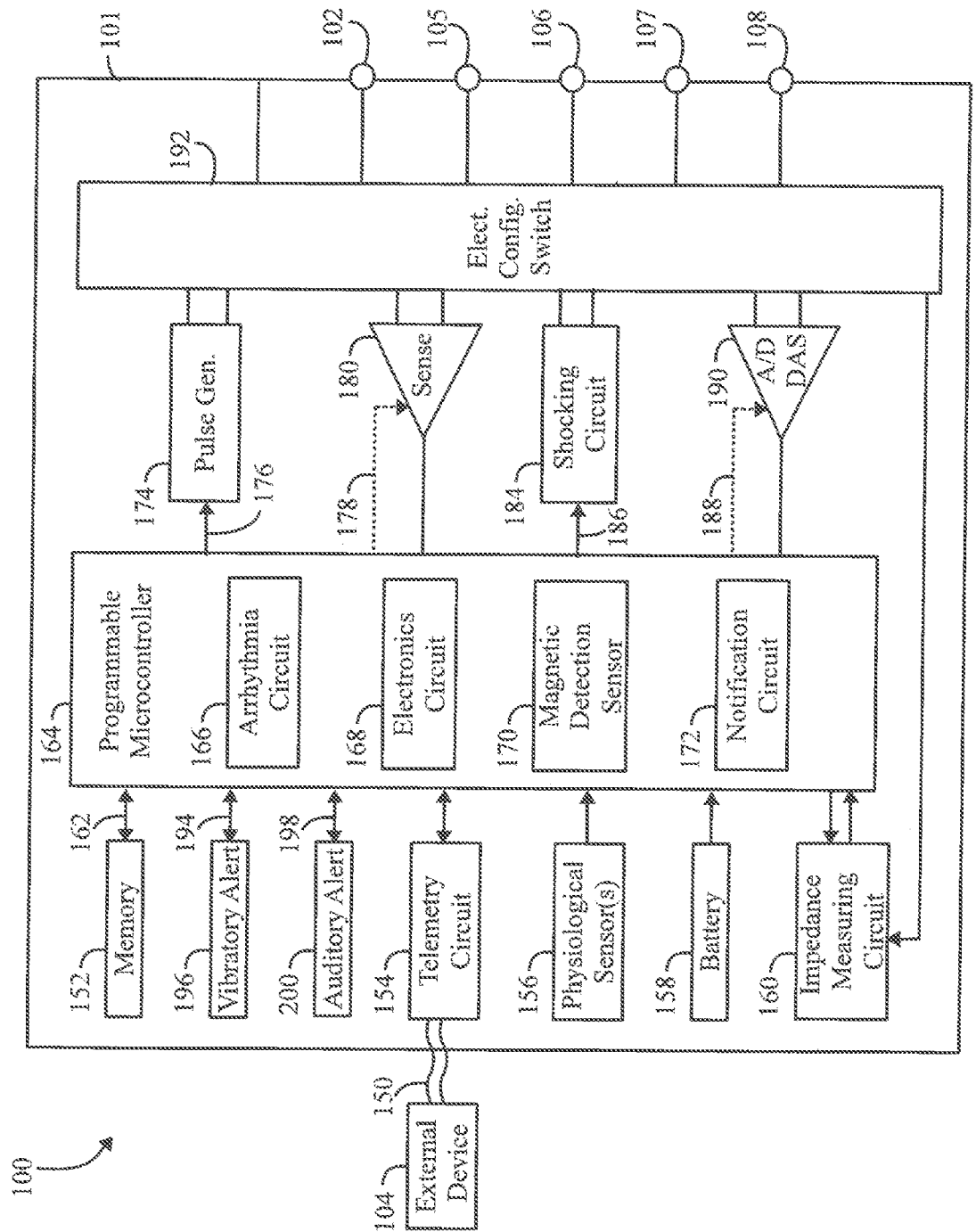
FIG. 2 illustrates a schematic view of an implantable medical device (IMD), in accordance with an embodiment.

FIG. 2 illustrates a schematic view of the IMD 100. The IMD 100 has a housing 101 to hold the electronic/computing components. The housing 101 (which is often referred to as the "can," "case," "encasing," or "case electrode") may be programmably selected to act as the return electrode for certain stimulus modes. The housing 101 further includes a connector (not shown) with a plurality of terminals 102, 105, 106, 107 and 108. The terminals may be connected to electrodes that are located in various locations within and about the heart. For example, the terminals may include: an electrode 102 to be coupled to a first electrode (e.g., a tip electrode) located in a first chamber; an electrode 105 to be coupled to a second electrode (e.g., tip electrode) located in a second chamber; an electrode 106 to be coupled to an electrode (e.g., ring) located in the first chamber; an electrode 107 to be coupled to an electrode located (e.g., ring electrode) in the second chamber; and an electrode 108 to be coupled to an electrode (e.g., coil) located in the SVC 116. The type and location of each electrode may vary. For example, the electrodes may include various combinations of a ring, a tip, a coil and shocking electrodes and the like.

The IMD 100 includes a programmable microcontroller 164 that controls various operations of the IMD 100, including cardiac monitoring and stimulation therapy. The microcontroller 164 includes a microprocessor (or equivalent control circuitry), one or more processors, RAM and/or ROM memory, logic and timing circuitry, state machine circuitry, and I/O circuitry.

The IMD 100 further includes an atrial and/or ventricular pulse generator 174 that generates stimulation pulses for connecting the desired electrodes to the appropriate 110 circuits, thereby facilitating electrode programmability. The switch 192 is controlled by a control signal 186 from the microcontroller 164.

A single pulse generator 174 is illustrated. Optionally, the IMD 100 may include multiple pulse generators, similar to the pulse generator 174, where each pulse generator is coupled to one or more electrodes and controlled by the microcontroller 164 to deliver select stimulus pulse(s) to the corresponding one or more electrodes.

The IMD 100 includes sensing circuitry 180 selectively coupled to one or more electrodes that perform sensing operations, through the switch 192 to detect the presence of cardiac activity in any chamber of the heart 105. The sensing circuitry 180 may include dedicated sense amplifiers, multiplexed amplifiers, shared amplifiers, and/or the like. It may further employ one or more low power, precision amplifiers with programmable gain and/or automatic gain control, bandpass filtering, threshold detection circuit to selectively sense the cardiac signal of interest, and/or the like. The automatic gain control enables the unit to sense low amplitude signal characteristics of atrial fibrillation. The switch 192 determines the sensing polarity of the cardiac signal by selectively closing the appropriate switches. In this way, the clinician may program the sensing polarity independent of the stimulation polarity.

The output of the sensing circuitry 180 is connected to the microcontroller 164 which, in turn, triggers or inhibits the pulse generator 174 in response to the absence or presence of cardiac activity. The sensing circuitry 180 receives a control signal 178 from the microcontroller 164 for purposes of controlling the gain, threshold, polarization charge removal circuitry (not shown), and the timing of any blocking circuitry (not shown) coupled to the inputs of the sensing circuitry.

In the example of FIG. 2, a single sensing circuit 180 is illustrated. Optionally, the IMD 100 may include multiple sensing circuits 180, similar to the sensing circuit 180, where each sensing circuit is coupled to one or more electrodes and controlled by the microcontroller 164 to sense electrical activity detected at the corresponding one or more electrodes. The sensing circuit 180 may operate in a unipolar sensing configuration or a bipolar sensing configuration.

The IMD 100 further includes an analog-to-digital (AID) data acquisition system (DAS) 190 coupled to one or more electrodes via the switch 192 to sample cardiac signals across any pair of desired electrodes. The IMD converter 190 is configured to acquire intracardiac electrogram signals, convert the raw analog data into digital data and store the digital data for later processing and/or telemetric transmission to an external device 104 (e.g., a programmer, local transceiver, or a diagnostic system analyzer). The A/D converter 190 is controlled by a control signal 188 from the microcontroller 164.

The microcontroller 164 includes an arrhythmia circuit 166 for analyzing cardiac activity signals sensed by the sensing circuit 180 and/or the A/D converter 190. The arrhythmia circuit 166 is configured to analyze cardiac signals sensed by the electrode and to deliver a therapy based on the cardiac signals. The arrhythmia detection circuit 166 declaring arrhythmias, in response to which, the microcontroller 164 determines an appropriate therapy. For example, responsive to the arrhythmia detection circuit 166 identifying a tachyarrhythmia, the microcontroller 164 directs the shocking circuit 184 to deliver a shock and/or directs the ATP pulse generator 174 to deliver an ATP therapy. The microcontroller 164 controls the timing of the stimulation pulses, the timing of refractory periods, blanking intervals, noise detection windows, evoked response windows, alert intervals, marker channel timing, and/or the like.

The microcontroller 164 is operably coupled to a memory 152 by a suitable data/address bus 162. The programmable operating parameters used by the microcontroller 164 are stored in the memory 152 and used to customize the operation of the IMD 100 to suit the needs of a particular patient. The operating parameters of the IMD 100 may be non-invasively programmed into the memory 152 through a telemetry circuit 154 in telemetric communication via communication link 150 (e.g., MICS, Bluetooth low energy, and/or the like) with the external device 104. The telemetry circuit 154 allows intracardiac electrograms and status information relating to the operation of the IMD 100 (as contained in the microcontroller 164 and/or memory 152) to be sent to the external device 104 through the established communication link 150.

The IMD 100 can further include one or more physiologic sensors 156. Such sensors are commonly referred to as "rate-responsive" sensors because they are typically used to adjust pacing stimulation rates according to the exercise state of the patient. However, the physiological sensor 156 may further be used to detect changes in cardiac output, changes in the physiological condition of the heart, or diurnal changes in activity (e.g., detecting sleep and wake states). Signals generated by the physiological sensors 156 are passed to the microcontroller 164 for analysis. While shown as being included within the unit 100, the physiologic sensor(s) 156 may be external to the IMD 100, yet still, be implanted within or carded by the patient. Examples of physiologic sensors might include sensors that, for example, sense respiration rate, pH of blood, ventricular gradient, activity, position/posture, minute ventilation (MV), and/or the like.

A battery 158 provides operating power to all of the components in the IMD 100. The battery 158 is capable of operating at low current drains for long periods of time, and is capable of providing a high-current pulses (for capacitor charging) when the patient requires a shock pulse (e.g., in excess of 2 A, at voltages above 2 V, for periods of 10 seconds or more). The battery 158 also desirably has a predictable discharge characteristic so that elective replacement time can be detected. As one example, the IMD 100 employs lithium/silver vanadium oxide batteries.

The IMD 100 further includes an impedance measuring circuit 160, which can be used for many things, including lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves; and so forth. The impedance measuring circuit 160 is coupled to the switch 192 so that any desired electrode may be used.

The microcontroller 164 further controls a shocking circuit 184 by way of a control signal 186. The shocking circuit 184 generates shocking pulses of low (e.g., up to 0.5 joules), moderate (e.g., 0.5-10 joules), or high energy (e.g., 11 to 40 joules), as controlled by the microcontroller 164. Such shocking pulses are applied to the patient's heart through shocking electrodes. It is noted that the shock therapy circuitry is optional and may not be implemented in the IMD 100.

In accordance with embodiments herein, the microcontroller 164 also includes (or is electrically coupled to) a magnetic detection sensor 170, an electronics circuit 168 and a notification circuit 172. The magnetic detection sensor 170 is configured to detect a magnetic field of an external magnetic source. The magnetic detection sensor 170 is configured to output a field detection signal indicative of, and based on, exposure of the magnetic detection sensor 170 to a magnetic field. By way of example only, the field detection signal may exhibit an amplitude that varies proportionally or based on another relation, to a strength of a magnetic field experienced by the magnetic detection sensor 170. Additionally or alternatively, the field detection signal may indicate a direction of flux density lines for the magnetic field experienced by the magnetic detection sensor 170. The electronics circuit 168 monitors the field detection signal for changes therein. For example, the electronics circuit 168 may determine when the field detection signal exceeds an amplitude threshold indicative of a magnetic field strength exceeding a corresponding field strength threshold. Additionally or alternatively, the electronics circuit 166 may determine when the field detection signal indicates a change in direction of the flux density lines of the magnetic field, thereby indicating a change in the position of the magnetic source. The electronics circuit 168 is configured to identify when a magnetic field is initiated, representing a magnetic field present (MFP) signals (also referred to as MFP state change). The electronics circuit 168 is further configured to identify when a magnetic field terminates, representing a magnetic field deactivation (MFD) signal (also referred to as MFD state change). The electronics circuit 168 may identify MFP and MFD signals (state changes) based on a comparison of the field detection signal to the amplitude threshold. For example, when the field detection signal exceeds the amplitude threshold, the electronics circuit 168 may declare an MFP signal. When the field detection signal falls below the amplitude threshold, the electronics circuit 168 may declare an MFD condition.

Additionally or alternatively, the electronics circuit 168 may declare the MFP signal when certain field stability criteria are satisfied. The electronics circuit 168 is configured to suspend the delivery of the therapy in response to detection of the magnetic field by the magnetic field sensor 170. For example, the electronics circuit 168 is configured to deliver a tachyarrhythmia therapy and to suspend the delivery of the tachyarrhythmia therapy in response to detection of the magnetic field by the magnetic field sensor 170. Similarly, when the field stability criteria are no longer satisfied, the electronics circuit 166 may declare the MFD signal. For example, the field stability criteria may provide that the magnetic detection sensor 170 detect a stable magnetic field for a predetermined stable field duration and/or having a predetermined stable magnetic field strength. As non-limiting examples, the strength of the stable field duration may be above 10 Gauss, and the length of time may be based on the strength of the magnetic, field above 10 Gauss between 1-10 seconds.

When the field stability criteria are satisfied, the electronics circuit 166 is configured to direct the microcontroller 164 to suspend delivery of a therapy. The electronics circuit 168 is also configured to trigger the notification circuit, by providing an MFP trigger or an MFD trigger. In response to an MFP trigger, the notification circuit 172 is configured to generate a notification output, in response to the detection of the magnetic field, indicating that the therapy has been suspended. In response to an MFD trigger, the notification circuit 172 is configured to generate a notification output indicating that the therapy has been resumed.

The electronics circuit 168, magnetic detection sensor 170 may determine that a magnetic field has been deactivated and/or terminated based on various criteria. For example, the magnetic detection sensor 170 may detect that the magnetic field is shifted in direction and/or strength. Additionally or alternatively, the electronics circuit 168 may determine that the magnetic detection sensor 170 no longer detects a magnetic field having a predetermined strength. When the electronics circuit 168 determines that the magnetic field has shifted in direction and/or strength by predetermined amounts, or no longer exhibits a minimum magnetic strength, the electronics circuit 168 provides the MFD trigger to the notification circuit 172. In response thereto, the notification circuit 172 may generate an MFD audio sequence and/or MFD vibration sequence that is different relative to the MFP audio sequence and/or vibration sequence. The MFD audio sequence and/or the vibration sequence provides an alert to the patient that the magnetic field is de-activated and/or terminated relative to the IMD 100. For example, the MFD audio sequence and/or the MFD vibration sequence may have different frequencies, amplitude, and/or the like relative to the MFP audio sequence and/or the MFP vibration sequence.

The magnetic detection sensor 170 may include a giant magnetoresistance (GMR) sensor, a reed switch, a Hall Effect sensor, and/or the like. For example, the magnetic detection sensor 170 is configured to detect the magnetic field of an external magnetic source proximate to the IMD 100. The external magnetic source generates the magnetic field, which is detected by the magnetic detection sensor 170.

Optionally, the magnetic detection sensor 170 may be configured to determine the MFP and/or MFD signals (e.g., conditions), and provide a corresponding MFP and/or MFD signals to the electronics circuit 168. For example, the magnetic field sensor 170 may detect the strength of the magnetic field and compare the magnetic field strength to a threshold. The magnetic field sensor 170 may only output an MFP signal when the magnetic field strength satisfies corresponding field stability criteria (e.g. exhibiting at least a predetermined field strength for a predetermined duration of time). When the field stability criteria are satisfied, the magnetic detection sensor 170 is configured to provide the MFP signal to the electronics circuit 168. For example, the strength and duration criteria may be a field greater than 10 Gauss, and/or for a duration such as between 1-10 seconds. The stable field criteria indicate a stable placement of the external magnetic source proximate to the IMD 100.

Optionally, the electronics circuit 168 may represent one or more status registers in the microcontroller 164 and/or memory 152, where the magnetic detection sensor 170 is configured to set the status register. For example, the magnetic detection sensor 170 may be configured provide MFP and/or MFD signals by setting/resetting an MFP status register and/or setting/resetting an MFD status register based on initiation and termination of a magnetic field with respect to the stable field criteria. The magnet detections sensor 170 adjusts the status register(s) to identify when the strength of the magnetic field exceeds the stable field duration and when the magnetic field is de-activated and/or terminated.

Additionally or alternatively, the electronics circuit 168 and/or magnetic detection sensor 170 may be configured to detect the movement of the magnetic field of the external magnetic source proximate to the IMD 100. For example, the electronics circuit 168 and/or magnetic detection sensor 170 may be configured to detect changes in the strength or direction of the magnetic field once an initial magnetic field has been established. When an initial magnetic field is established and then the field strength drops below a predetermined threshold, the electronics circuit 168 and/or magnetic detection sensor 170 identify the change to represent movement of the magnet and declare the magnetic field to be de-activated and/or terminated. The electronics circuit 168 and/or magnetic detection sensor 170 trigger an MFD alert that the magnetic field is de-activated and/or terminated. Responsive to the trigger from the magnetic detection sensor 170, the electronics circuit 168 generates an alert to the notification circuit 172 to provide the audio sequence and/or the vibration sequence to notify the patient the magnetic field is de-activated and/or terminated.

Optionally, the electronics circuit 168 and/or magnetic detection sensor 170 may identify a magnet adjustment condition based on magnetic field strength, direction and duration. For example, a magnet adjustment condition may occur when a magnetic source is being shifted, but not intentionally entirely removed. Electronics circuit 168 and/or magnetic detection sensor 170 may identify the magnet adjustment condition, and generate a corresponding magnet adjustment alert to inform the user that the magnetic source is being shifted. The magnet adjustment alert may afford the user the opportunity to reapply the magnetic source in a desired manner without inadvertently allowing therapy to be resumed.

The IMD 100 includes at least one of an auditory alert 200 and/or vibratory alert 196 that may be activated by the microcontroller 164 based on the MFP, MFD and magnet adjustment conditions/triggers. The microcontroller 164 emits control signals 194, 198 to activate a vibrator 196 and/or an auditory alert 200.

The vibratory alert 196 includes an electric motor that includes an offset and/or additional weight on the shaft. For example, the offset and/or additional weight on the shaft generates vibration to the IMD 100. The control signal 194 may output a series of digital pulses and/or analog pulses that form a vibration sequence. The vibration sequence includes a series of vibrations generated by the vibratory alert 196 formed by the frequencies, amplitudes, and/or the like of the control signal 194. Separate vibration sequences are defined to alert a patient of various conditions, such as the MFP signal, MFD signal and magnet adjustment condition.

The auditory alert 200 includes at least one of a speaker, a piezoelectric speaker, and/or the like. The control signal 198 may include a series of digital pulses and/or analog pulses that generate the auditory alert 200 on the speaker. The auditory alert 200 represents a series of tones that define an audio sequence. The audio sequence includes a set of audio signals generated by the audio alert 200 formed by the frequencies, amplitudes, and/or the like of the control signal 198. Separate audio sequences are defined to alert a patient of various conditions, such as the MFP signal, rum signal and magnet adjustment condition. Optionally, the vibrator 196 and/or the auditory alert 200 may be utilized concurrently and/or simultaneously based on the control signals 194 and 198 from the microcontroller 164.

Figure 3:
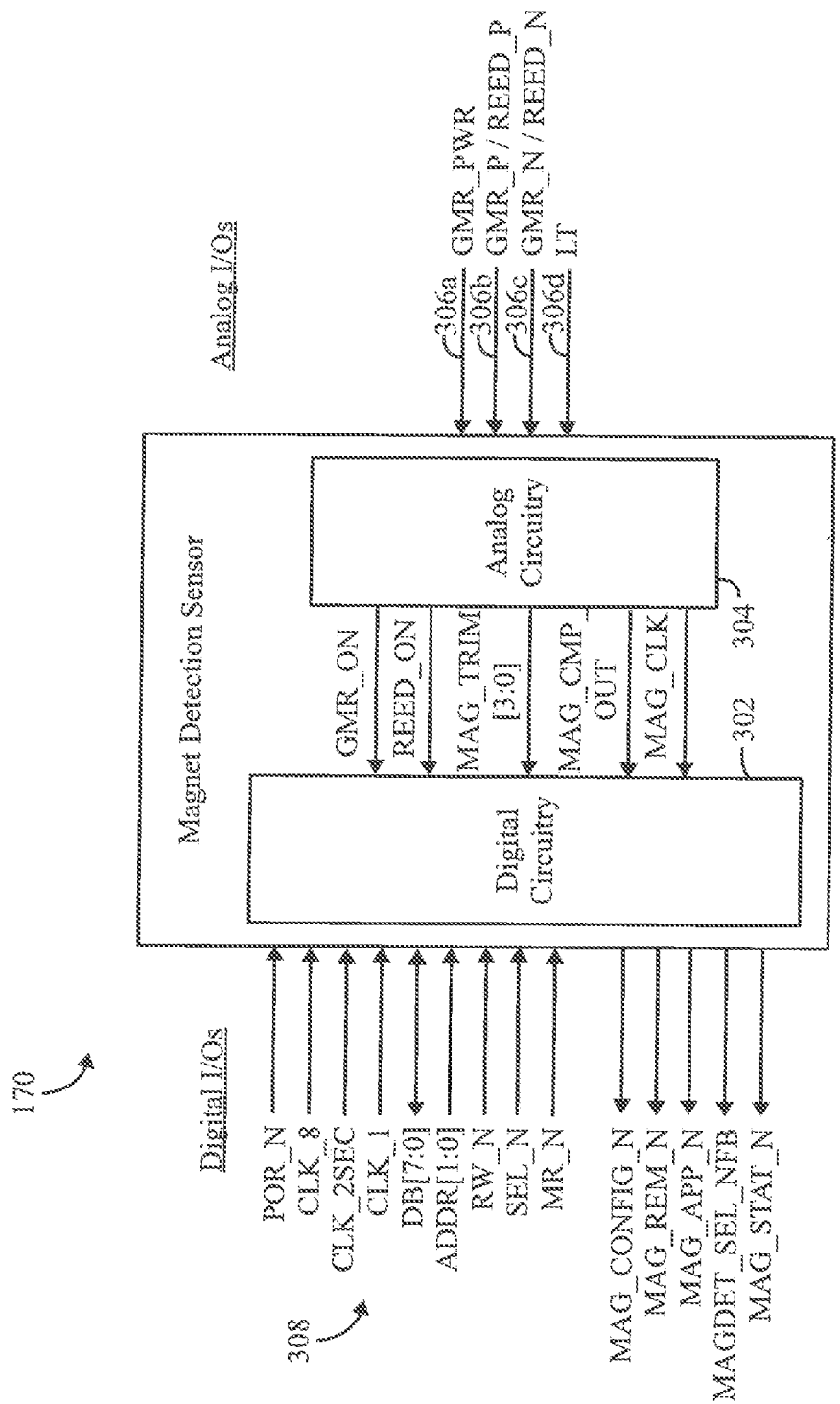
FIG. 3 illustrates a schematic view of an external magnet detected by the magnetic detection sensor, in accordance with an embodiment.

FIG. 3 illustrates a schematic view of the magnetic detection sensor 170. For example, the magnet the magnetic detection sensor 170 includes an analog circuitry 304 and the magnetic detection sensor 170 is shown operably coupled to a reed switch. The magnetic detection sensor 170 includes analog circuitry 304 and/or digital circuitry 302. The analog circuitry 304 is operably coupled to the reed switch. The reed switch includes analog inputs/outputs for the analog circuitry 304. For example, the analog circuitry 304 provides electrical power 306a, a positive voltage 306b, a negative voltage 306c, and/or a level transmitter 306d. The analog circuitry 304 is operably coupled to the digital circuitry 302. The analog circuitry 304 receives electrical power, activation of the reed switch, and/or the like from the digital circuitry 302. The analog circuitry 304 outputs the measurements of the reed switch to the digital circuitry 302. The digital outputs 308 of the digital circuitry 302 are received by the microcontroller 164. For example, the microcontroller 164 may relay the digital outputs 308 to the electronics circuit 168.

Figure 4:
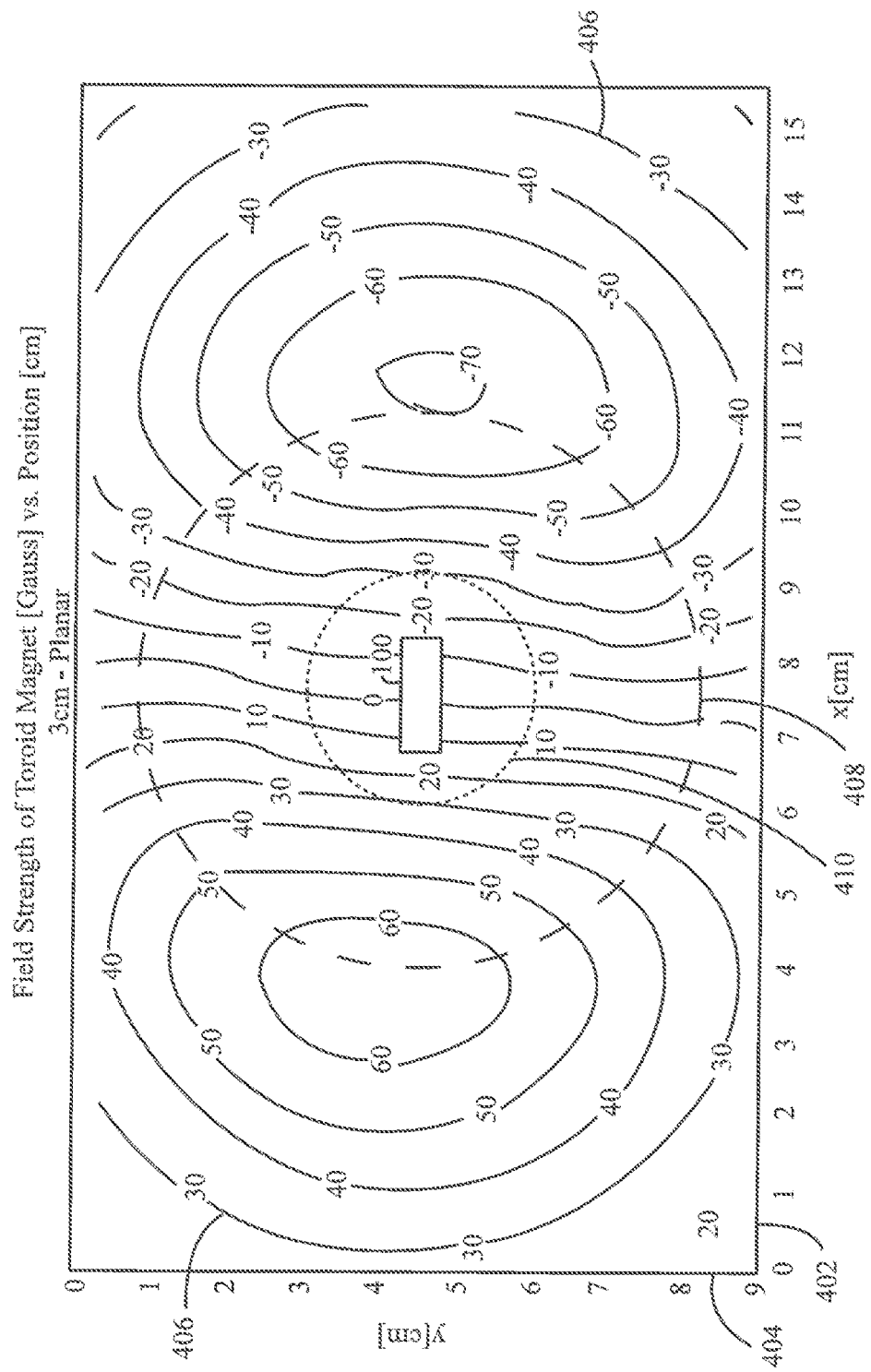
FIG. 4 illustrates magnetic field lines of an external magnet detected by the magnetic detection sensor, in accordance with an embodiment.

FIG. 4 illustrates magnetic field lines 406 of an external magnet source 408 detected by the magnetic detection sensor 170. The magnetic field lines 406 are shown along horizontal and vertical axes 402, 404. The horizontal axis 402 is shown alongside the IMD 100. For example, the horizontal axis 402 may represent the axis of the IMD 100 for the detection of the magnetic field lines 406. The horizontal axis 402 and/or the vertical axis 404 are shown as a centimeter relative to the IMD 100.

The external magnet source 408 is shown being a toroid magnet. Optionally, the external magnet source 408 may have a larger and/or smaller interior circumference 410 than shown in FIG. 4. For example, the external magnet includes the interior circumference 410 that includes one or more null zones. Within the one or more null zones of the interior circumference 410, the magnetic field may be 0 Gauss.

The external magnet source 408 is repositioned relative to the IMD 100. For example, the IMD 100 may be positioned within the interior circumference 410. The magnetic detection sensor 170 detects the magnetic field lines 406 of the external magnet source 408. For example, the magnetic detection sensor 170 determines whether the MFP signal exceeds the stable field duration. The magnetic detection sensor 170 measures the magnetic field lines 406 generated by the external magnet source 408. The magnetic detection sensor 170 may measure the magnetic field strength and/or an amount of time of the magnetic field lines 406. For example, the magnetic detection sensor 170 identifies that the magnetic field lines 406 have reached and/or exceed the stable field duration. For example, the magnetic detection sensor 170 measures the strength of the magnetic field lines 406. The magnetic detection sensor 170 determines if the strength of the magnetic field exceeds the stable field duration (e.g., above 10 Gauss, and/or above 10 Gauss for 1-10 seconds) to provide the MFP signal. Responsive to the magnetic detection sensor 170 reaching the MFP signal, the magnetic detection sensor 170 triggers the electronics circuit 168. Based on the trigger, the electronics circuit 168 is configured to trigger the notification circuit 172 to generate the field detected indicator. For example, the field detected indicator may represent an output using the control signals 194 and 198 to the vibrator 196 and/or audio alert 200 that the strength of the magnetic field exceeds the stable field duration.

Additionally or alternatively, the magnetic detection sensor 170 may detect the magnetic field lines 406 are below the field stability criteria. For example, the magnetic detection sensor 170 determines that the magnetic field strength and/or an amount of time of the mimetic field lines 406 are below the field stability criteria. The magnetic detection sensor 170 identifies the magnetic field lines 406 are de-activated and/or terminated. Responsive to the magnetic detection sensor 170 not reaching the field stability criteria, the magnetic detection sensor 170 triggers the electronics circuit 168. For example, the trigger represents the termination of the magnetic field ones 406. The electronics circuit 168 is configured to trigger the notification circuit 172 to generate the field detected indicator. For example, the field loss indicator may represent an output using the control signals 194 and 198 to the vibrator 196 and/or auditory alert 200 to output the vibration sequence and/or the audio sequence that is different from the trigger of the stable field duration. The field loss indicator indicates that the magnetic detection sensor 170 has detected the magnetic field is de-activated and/or terminated.

Figure 5:
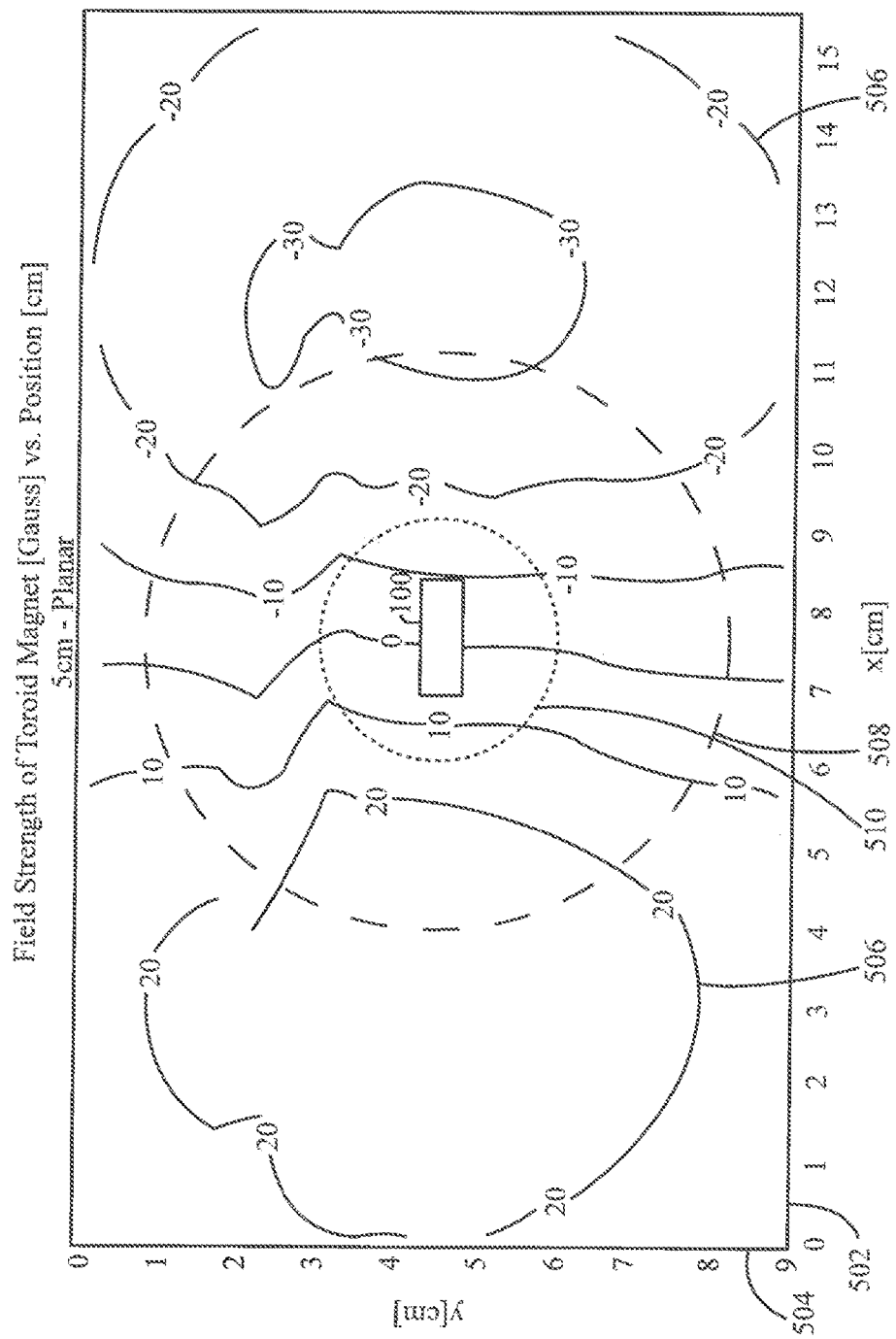
FIG. 5 illustrates magnetic field lines of an external magnet detected by the magnetic detection sensor, in accordance with an embodiment.

FIG. 5 illustrates magnetic field lines 506 of an external magnet source 508 detected by the magnetic detection sensor 170. The magnetic field lines 506 are shown along horizontal and vertical axes 502, 504. The horizontal axis 502 is shown alongside the IMD 100. For example, the horizontal axis 502 may represent the axis of the IMD 100 for the detection of the magnetic field lines 506. The horizontal axis 502 and/or the vertical axis 504 are shown as a centimeter distance from the IMD 100.

The external magnet source 508 is shown being a torpid magnet. For example, the external magnet source 508 is shown having an interior circumference 510 that is larger than the external magnet source 408 shown in FIG. 4. Similar to and/or the same as the external magnet source 408, the external magnet source 508 includes one or more null zones. Within the one or more null zones of the interior circumference 510, the magnetic field may be 0 Gauss.

The external magnet source 508 is repositioned relative to the IMD 100. For example, the IMD 100 may be positioned within the interior circumference 510. The magnetic detection sensor 170 detects the magnetic Held lines 506 of the external magnet source 508. For example, the magnetic detection sensor 170 determines whether the MFP signal exceeds the stable field duration. The magnetic detection sensor 170 measures the magnetic field fines 506 generated by the external magnet source 508. The magnetic field sensor 170 may measure the magnetic field strength and/or an amount of time of the magnetic field lines 506. For example, the magnetic detection sensor 170 identifies that the magnetic field lines 506 have reached and/or exceed the stable field duration. Responsive to the magnetic detection sensor 170 reaching the MFP signal, the magnetic detection sensor 170 triggers the electronics circuit 168. Based on the trigger, the electronics circuit 168 is configured to trigger the notification circuit 172 based on the detection of the magnetic field by the magnetic detection sensor 170. For example, the magnetic field detection may represent an output using the control signals 194 and 198 to the vibratory alert 196 and/or auditory alert 200.

Figure 6:
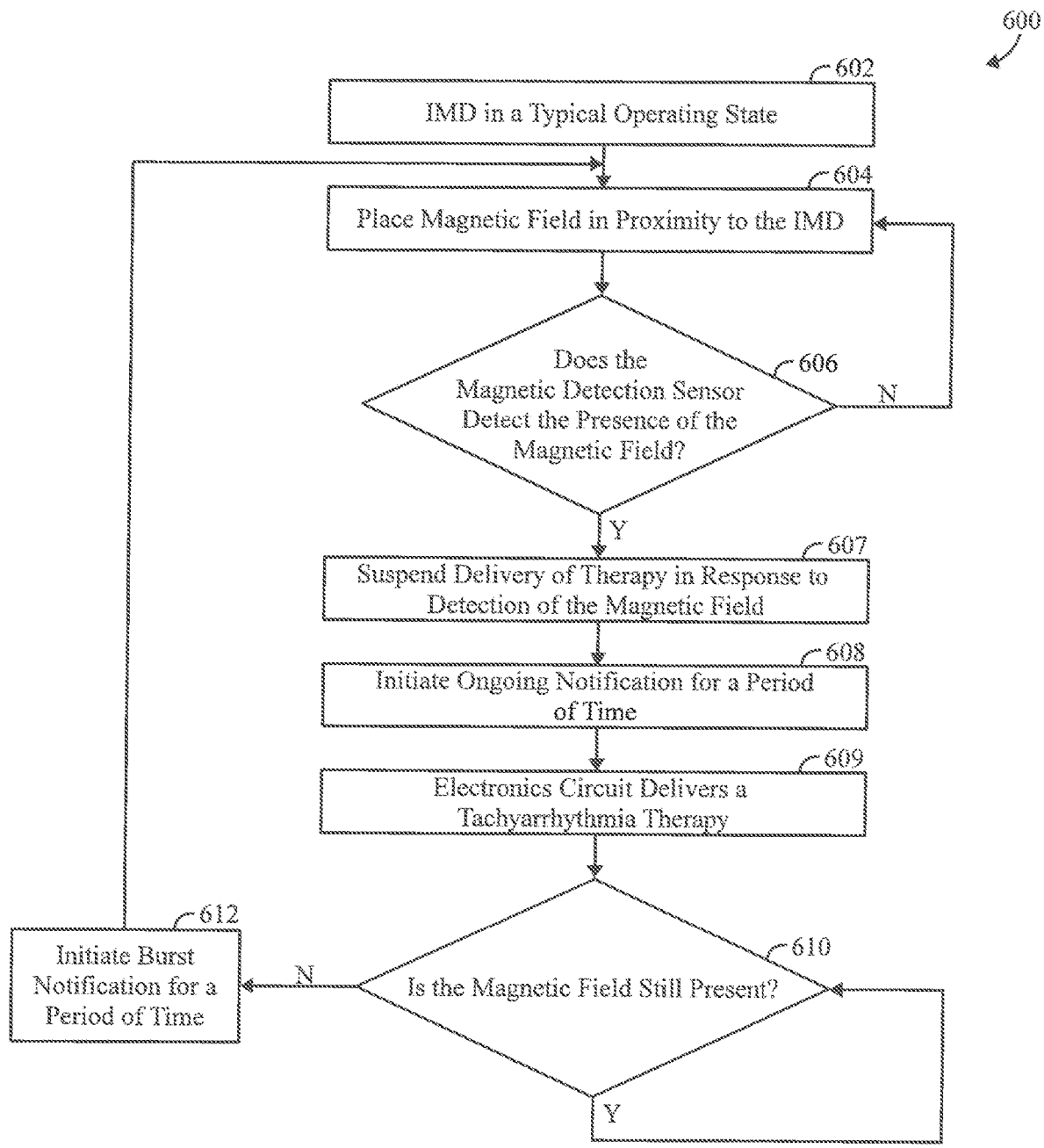
FIG. 6 illustrates a flowchart of a method to detect a magnetic field, in accordance with an embodiment.

FIG. 6 illustrates a flowchart of a method 600 to detect a magnetic field, in accordance with an embodiment. The method 600, for example, may employ or be performed by structures or assets of various embodiments (e.g., systems and/or methods and/or process flows) discussed herein. In various embodiments, certain steps may be omitted or added, certain steps may be combined, certain steps may be performed concurrently, certain steps may be split into multiple steps, or certain steps may be performed in a different order. As one nonlimiting example, various operations are described as being performed by the magnetic detection sensor 170, although it is understood that such operations may also be performed by the electronics circuit 168 and/or other structures.

Beginning at 602, the IMD 100 is in a typical operating state. For example, the IMD 100 is positioned within the patient. The external magnetic source 408, 508 is being positioned proximate to the IMD 100. At 604, the external magnetic source 408, 508 that generates the magnetic field is positioned proximate to the IMD 100. For example, the magnetic detection sensor 170 is configured to detect the magnetic field generated by the external magnetic source 408, 508. The magnetic detection sensor 170 is configured to provide the MFP signal based on a strength and/or that exceeds a stable field duration.

At 606, the magnetic detection sensor 170 determines if the external magnetic source 408, 508 detects the presence of the magnetic field for the field stability criteria. For example, the magnetic detection sensor 170 may measure the strength, and/or the strength of the magnetic field for an amount of time, generated by the external magnetic source 408, 508. The magnet section sensor 170 determines the strength, and/or strength of the magnetic field for an amount of time, of the magnetic field. Responsive to the magnetic detection sensor 170 being above 10 Gauss and/or, the strength of 10 Gauss during a time period for 1-10 seconds, the magnetic detection sensor 170 determines the magnetic field exceeds the stable field duration. For example, the magnetic detection sensor 170 transmits the trigger to the electronics circuit 168. The trigger may represent a notification output to the electronics circuit 168. For example, the trigger may include at least one of the MFP signal, a digital pulse, an analog pulse, and/or the like.

Additionally or alternatively, the magnetic detection sensor 170 detects a termination of the magnetic field generated by the external magnetic source 408, 508. For example, the magnetic detection sensor 170 may measure the strength (e.g., magnitude) and/or the duration to determine whether the magnetic field has satisfied the field stability criteria. In the present example, the electronics circuit 168 and/or magnetic detection sensor 170 may determine that the magnetic field strength is below 10 Gauss and/or the magnetic field strength did not remain above 10 Gauss for at least 10 seconds, and thus declare the magnetic field to have terminated (and MFD condition). In response thereto, the electronics circuit 168 and/or magnetic detection sensor 170 transmits the MFD trigger. If the process determines that the magnetic field is de-activated and/or terminated, the method 600 returns to the operation 604.

At 607, the microcontroller 164 suspends delivery of therapy in response to detection of the magnetic field. For example, the microcontroller 164 instructs the pulse generator 174 to stop generating stimulation pulses for delivery by the one or more electrodes 102, 105, 106, 107, 108. The microcontroller 164 stops sending control signals to the control signal 176. For example, the microcontroller 164 suspends delivery of therapy based on the notification signal received from the magnet notification sensor 170.

If the magnetic detection sensor 170 determines that the magnetic field exceeds the stable field duration, then at 608, the electronics circuit 168 Initiates ongoing patient notification for a period of time. For example, the period of time may be greater than 10 seconds (e.g., 16 seconds). The magnetic detection sensor 170 may transmit a trigger to the electronics circuit 168. The trigger may represent that the magnetic field exceeds the stable field duration. Optionally, the trigger may represent the MFP signal to the electronics circuit 168.

At 609, responsive to the magnetic field detection, the electronics circuit 168 is configured to deliver a tachyarrhythmia therapy. The electronics circuit 168 is configured to suspend the delivery of the tachyarrhythmia therapy in response to detection of the magnetic field by the magnetic field sensor 170. The magnetic detection sensor 170 detects a magnet is place over a region of a patient proximate to an implant location of the IMD 100. The magnetic detection sensor 170 detects the MFP signal, which exceeds the stable field duration. For example, the electronics circuit 168 is configured to deliver a tachyarrhythmia therapy and to suspend the delivery of the tachyarrhythmia therapy in response to detection of the magnetic field by the magnetic field sensor 170.

At 610, the magnetic detection sensor 170 determines if the magnetic field is still present. For example, the magnetic detection sensor 170 measures the strength and/or the strength for the amount of time the strength exceeds the stable field duration.

If the magnetic detection sensor 170 determines the magnetic field exceeds the stable field duration, the method 600 returns to the operation 610.

If the magnetic detection sensor 170 determines the magnetic field does not exceed the stable field duration, then at 612, the notification circuit 172 initiates a burst patient notification for a period of time. For example, the period of time may be greater than 2 seconds. The notification circuit 172 provides a vibration sequence and/or audio sequence to the vibrator 196 and/or auditory alert 200, respectively. For example, the notification circuit 172 the vibration sequence and/or audio sequence may be based on the control signals 194 and 198.

Figure 7:
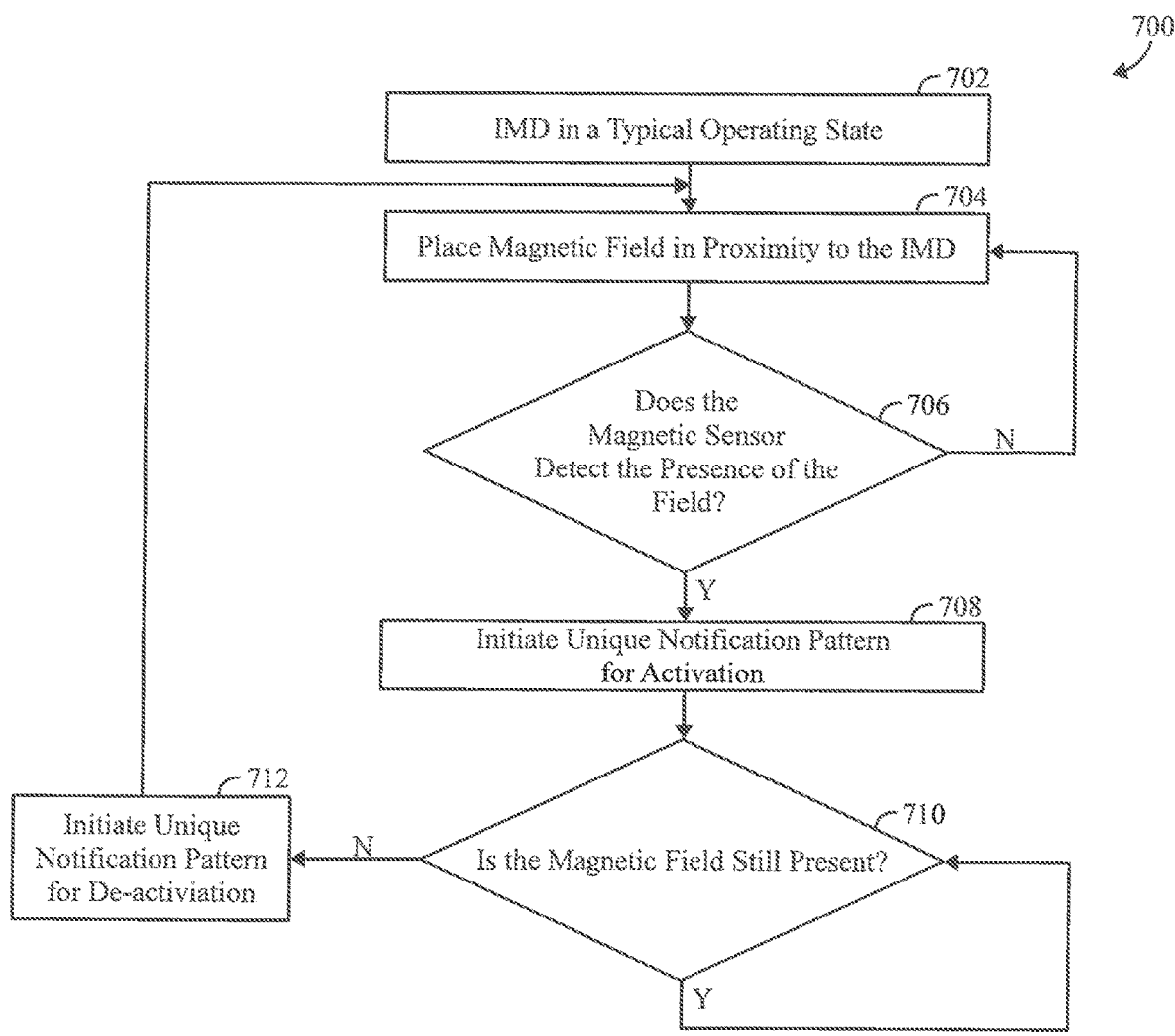
FIG. 7 illustrates a flowchart of a method to detect a magnetic field, in accordance with an embodiment.

FIG. 7 illustrates a flowchart of a method 700 to detect a magnetic field, in accordance with an embodiment. The method 700, for example, may employ or be performed by structures or assets of various embodiments (e.g., systems and/or methods and/or process flows) discussed herein. In various embodiments, certain steps may be omitted or added, certain steps may be combined, certain steps may be performed concurrently, certain steps may be split into multiple steps, or certain steps may be performed in a different order.

Beginning at 702, the IMD 100 is in a typical operating state. For example, the IMD 100 is positioned within the patient.

At 704, the external magnetic source 408, 508 that generates the magnetic field is positioned proximate to the IMD 100. For example, the magnetic detection sensor 170 is configured to detect the magnetic field generated by the external magnetic source 408, 508. The magnetic detection sensor 170 is configured to provide the MFP signal based on a strength that exceeds the stable field duration.

At 706, the magnetic detection sensor 170 determines if the external magnetic source 408, 508 detect the presence of the magnetic field. For example, the magnetic detection sensor 170 may measure the strength and/or an amount of time of the strength of the magnetic field generated by the external magnetic source 408, 508. The magnet detection source 170 determines that the strength of the magnetic field and/or the strength of the magnetic field for the amount of time of the magnetic field. Responsive to the magnetic detection sensor 170 being above 10 Gauss and/or the strength of 10 Gauss during a time period for 1-10 seconds, the magnetic detection sensor 170 determines that the strength of the magnetic field exceeds the stable field duration. For example, the magnetic detection sensor 170 transmits the trigger to the electronics circuit 168.

Additionally or alternatively, the magnetic detection sensor 170 detects the de-activation and/or termination of the magnetic field generated by the external magnetic source 408, 508. For example, the magnetic detection sensor 170 may measure the strength and/or an amount of time of the strength of the magnetic field generated by the external magnetic source 408, 508. The magnetic detection sensor 170 determines the strength in/or the strength of the magnetic field for the amount of time that exceeds the stable field duration. Responsive to the magnetic detection sensor 170 detecting the strength of the magnetic field below 10 Gauss and/or the strength of the magnetic field below 10 Gauss during an amount of time. The magnetic detection sensor 170 determines the magnetic field is de-activated in/or terminated. For example, the magnetic detection sensor 170 transmits the trigger representing a termination in/or de-activation of the magnetic field to the electronics circuit 168.

If the magnetic detection sensor 170 determines that the magnetic field is de-activated and/or terminated, the methods 700 returns to the operation 704.

If the magnetic detection sensor 170 determines that the magnetic field exceeds the stable field duration, then at 708, the electronics circuit 168 initiate a unique patient notification pattern for activation. The trigger may represent that the magnetic field exceeds the stable field duration. For example, the trigger may represent the MFP signal to the electronics circuit 168. The unique patient notification may represent the vibration sequence and/or the alert sequence that indicate the magnetic detection sensor 170 identified the magnetic field that exceeds the stable field duration. For example, the unique patient notification is different than the vibration sequence and/or the alert sequence for the de-activation and/or termination of the mimetic field.

At 710, the magnetic detection sensor 170 determines that the magnetic field is still present. For example, the magnetic detection sensor 170 measures the strength and/or the strength of an amount of time of the magnetic field that exceeds the stable field duration.

The magnetic detection sensor 170 determines the magnetic field exceeds the stable field duration, the method 700 returns to the operation 710. The magnetic detection sensor 170 determines the magnetic field does not exceed the stable field duration, then at 710, the notification circuit 172 initiates a unique patient notification pattern for de-activation and/or termination. For example, the magnetic detection sensor determines that the magnetic field has the strength and/or is below the strength for a period of time below this stable field duration. The magnetic detection sensor 170 sends the trigger to the electronics circuit 168. The trigger may include the termination of the magnetic field generated by the external magnetic source 408, 508. The electronics circuit 168 trigger the notification circuit 172. The notification circuit 172 provides a vibration sequence and/or audio sequence to the vibrator 196 and/or auditory alert 200, respectively. For example, the notification circuit 172 the vibration sequence and/or audio sequence may be based on the control signals 194 and 188. The unique sequence representing the termination of the magnetic field is different than the unique sequence of the operation at 708. For example, the vibration sequence and/or the audio sequence has a different frequency, amplitude, and/or the like relative to the unique patient notification for the detection of the magnetic field strength that exceeds the stable field duration.

At 712, the notification circuit 172 initiates a unique patient notification pattern for de-activation. The microcontroller 164 triggers the patient notification circuit 172 to deliver the unique patient notification for a period of time. The set period of time may be less than 5 seconds (e.g., such as 2 seconds). The stimulus may include the control signals 194, 198 delivered to the vibrator 196 and/or the auditory alert 200 from the notification circuit 172. For example, the control signals 194, 198 may form a vibration sequence and/or auditory sequence. The control signals 194, 198 may have a set of frequencies, amplitudes, and/or the like that indicate the magnetic field is de-activated and/or terminated.

Figure 8:
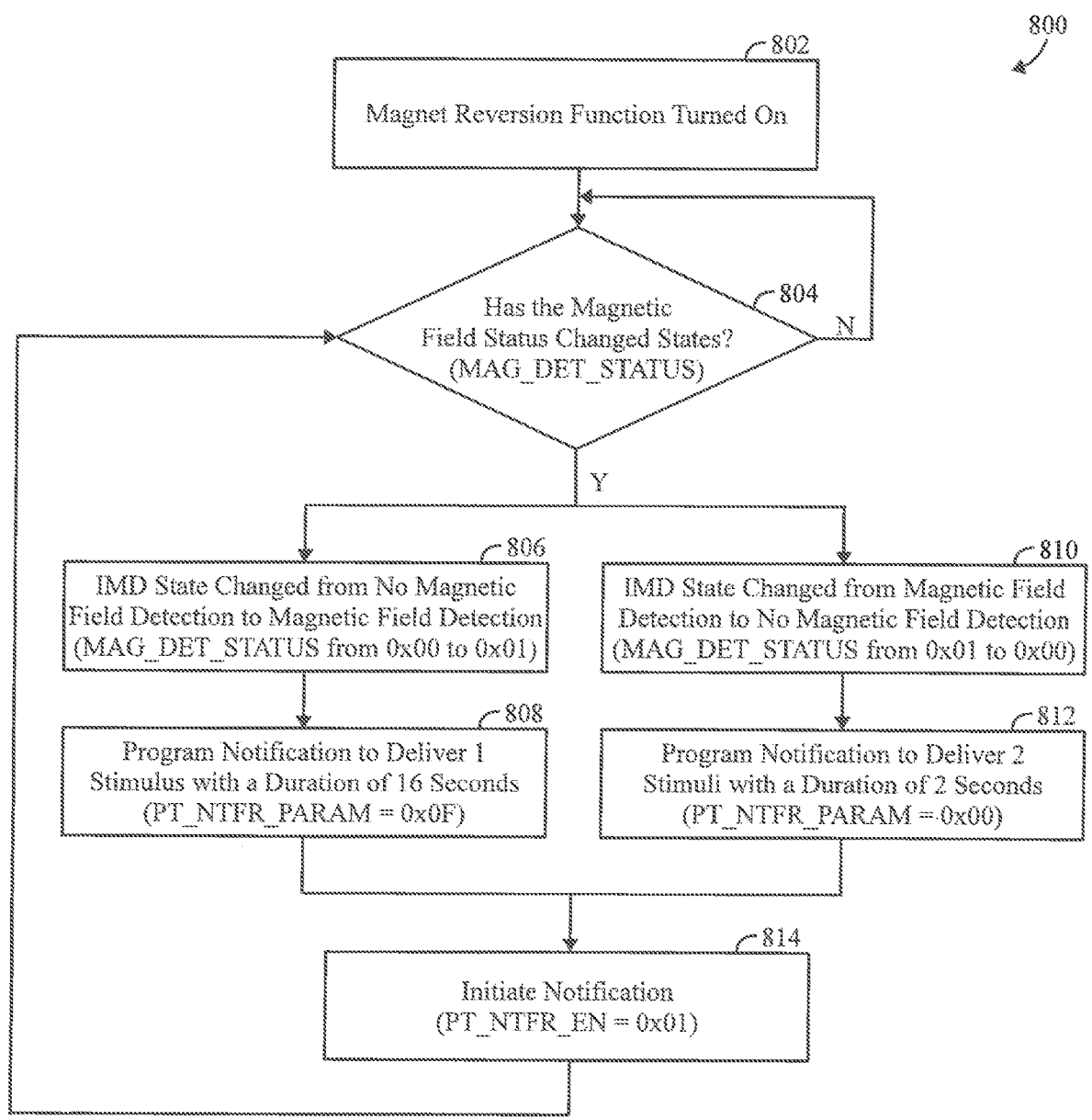
FIG. 8 illustrates a flowchart of a method to detect a magnetic field, in accordance with an embodiment.

FIG. 8 illustrates a flowchart of a method 800 to detect a magnetic field, in accordance with an embodiment. The method 800, for example, may employ or be performed by structures or assets of various embodiments (e.g., systems in/or methods and/or process flows) discussed herein. In various embodiments, certain steps may be performed in a different order. For example, the method 800 adjusts a status register of the microcontroller 164 and/or the memory 152 based on the detection of the magnetic field by the magnetic detection sensor 170. For example, the status register includes the MAG_DET_STATUS, which may be based on the MFP signal triggered by the magnetic detection sensor 170.

Beginning at 802, the magnet reversion function of the magnetic detection sensor 170 is turned on. For example, the magnetic detection sensor 170 is provided electrical power from the microcontroller 164. The Hall Effect sensor, the GMR sensor, the Reed switch, and/or the like, is provided electrical power from the microcontroller 164. The magnetic detection sensor 170 is activated, such that the magnetic detection sensor 170 may detect the magnetic field of an external magnet source 408, 508.

At 804, the magnetic detection sensor 170 determines whether the magnetic field status changed. For example, the magnetic detection sensor 170 identifies the strength and/or duration of the magnetic field generated by the external magnet source 408, 508. The magnetic detection sensor 170 determines whether the magnetic field exceeds a stable field duration. For example, the stable field duration includes the strength of the magnetic field above 10 Gauss and/or the strength above 10 Gauss for the duration of time between 1-10 seconds. The magnetic detection sensor 170 provides the MFP signal when the magnetic field has the strength that exceeds the stable field duration. For example, the magnetic detection sensor 170 triggers the electronics circuit 168, responsive to the magnetic field having the strength that exceeds the stable field duration.

If the magnetic field status has not changed, the method 800 returns to the operation 804. For example, responsive to the magnetic detection sensor 170 not detecting the magnetic field, the method returns the operation 804. The external magnetic source 408, 508 may not be proximate to and/or currently being installed into the patient. For example, the magnetic fields may not be detected by the magnetic detection sensor 170.

If the magnetic field status has identified the magnetic field having a strength (e.g., magnitude) that exceeds the stable field duration, then at 806, the IMD 100 changes the status register from no magnetic field detection to a magnetic field detection. For example, the magnetic detection sensor 170 adjusts the status register MAG_DET_STATUS of the microcontroller 164 and/or the memory 152 to 0x01. The change in the status register indicates that the magnetic field is detected and exceeds the stable field duration, Responsive to the change in the status register, the electronics circuit 168 receives the MFP signal from the magnetic detection sensor 170.

At 808, the microcontroller 164 triggers the patient notification to deliver a stimulus with a duration of a period of time. For example, the electronics circuit 168 is configured to direct the notification circuit 172 to provide the patient notification. The notification circuit 172 provides the control signals 194, 198 to the vibrator 196 and/or the auditory alert 200, respectively. For example, the control signals 194, 198 generate a vibration sequence and/or the audio sequence that indicates the magnetic field is detected. The control signals 194, 198 may have a set of frequencies, amplitudes, and/or the like that indicate the magnetic field is detected.

If the magnetic field is de-activated and/or terminated, then at 810, the notification circuit 172 delivers a stimulus for a duration for a set period of time. For example, the magnetic detection sensor 170 adjusts the status register MAG_DET_STATUS of the microcontroller 164 and/or the memory 152 to 0x00. The change in the status register indicates that the magnetic field is de-activated and/or terminated. For example, the magnetic field does not have a strength that exceeds the stable field duration. Responsive to the change in the status register, the electronics circuit 168 receives the trigger from the magnetic detection sensor 170 that the magnetic field is de-activated and/or terminated.

If the magnetic field status has identified the magnetic field having been terminated and/or de-activated, then at 812, the microcontroller 164 triggers the patient notification circuit 172 to deliver to stimulus with a duration of a period of time. The set period of time may be less than 5 seconds (e.g., such as 2 seconds). The stimulus may include the control signals 194, 198 delivered to the vibrator 196 and/or the auditory alert 200 from the notification circuit 172. For example, the control signals 194, 198 may form a vibration sequence and/or auditory sequence. The control signals 194, 198 may have a set of frequencies, amplitudes, and/or the like that indicate the magnetic field is de-activated and/or terminated.

At 814, the notification circuit 172 initiates the patient notification. For example, the notification circuit 172 supplies the control signals 194, 198 to the vibrator 196 and/or the auditory alert 200, respectively. The notification circuit 172 defines the vibration sequence and/or the auditory sequence using the control signals 194, 198. For example, the patient notification for the detection of the magnetic field has a different vibration sequence and/or the auditory sequence relative to the de-activation and/or termination of the magnetic field. The vibration sequence and/or the audio sequence defined by the control signals 194, 198 may have different frequencies, amplitudes, and/or the like relative to each other.

Closing Statements it should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

As will be appreciated by one skilled in the art, various aspects may be embodied as a system, method or computer (device) program product. Accordingly, aspects may take the form of an entirely hardware embodiment or an embodiment including hardware and software that may all generally be referred to herein as a "circuit," "module" or "system." Furthermore, aspects may take the form of a computer (device) program product embodied in one or more computer (device) readable storage medium(s) having computer (device) readable program code embodied thereon.

Any combination of one or more non-signal computer (device) readable medium(s) may be utilized. The non-signal medium may be a storage medium. A storage medium may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a dynamic random access memory (DRAM), a read-only memory (ROM), an erasable programmable read-only memory (EPROM or Rash memory), a portable compact disc read-only memory (CD-ROM), an optical storage device, a magnetic storage device, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of network, including a local area network (LAN) or a wide area network (WAN), or the connection may be made through other devices (for example, through the Internet using an Internet Service Provider) or through a hard wire connection, such as over a USB connection. For example, a server having a first processor, a network interface, and a storage device for storing code may store the program code for carrying out the operations and provide this code through its network interface via a network to a second device having a second processor for execution of the code on the second device.

Aspects are described herein with reference to the Figures, which illustrate example methods, devices and program products according to various example embodiments. These program instructions may be provided to a processor of a general purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

The units/modules/applications herein may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally or alternatively, the modules/controllers herein may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The units/modules/applications herein may execute a set of instructions that are stored in one or more storage elements, in order to process data. The storage elements may also store data or other information as desired or needed. The storage element may be in the form of an information source or a physical memory element within the modules/controllers herein. The set of instructions may include various commands that instruct the modules/applications herein to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects or order of execution on their acts.

What is claimed is:

1. An implantable medical device (IMD), comprising:
    at least one electrode;
    a magnetic detection sensor configured to detect a magnetic field of a external magnetic source responsive to placement of the external magnetic source over a region proximate to an implant location of the IMD;
    a notification circuit;
    an arrhythmia circuit configured to analyze cardiac signals sensed by the electrode and to deliver a therapy based on the cardiac signals; and
    an electronics circuit configured to suspend the delivery of the therapy in response to a determination that the magnetic field satisfies strength and duration field stability criteria that indicate a stable placement of the external magnetic source proximate to the IMD;
    wherein the electronics circuit is configured to trigger the notification circuit to generate a notification output in response to the determination that the magnetic field satisfies field stability criteria and that the therapy has been suspended, and wherein the magnetic detection sensor is configured to detect the magnetic field that includes multiple null zones, the magnetic detection sensor configured to detect when the IMD is located at least partially in one of the null zones.

2. The device of claim 1, wherein the magnetic detection sensor is configured to provide a magnetic field present (MFP) signal to the electronics circuit when the magnetic detection sensor experiences a magnetic field that satisfies the strength and duration field stability criteria indicating the stable placement of the external magnetic source proximate to the implantable medical device.

3. The device of claim 2, wherein the electronics circuit is configured to trigger the notification circuit to generate a field detected indicator, as the notification, when the MFP signal is maintained for a period of time that exceeds a stable field duration between 1-10 seconds.

4. The device of claim 1, wherein the electronics circuit is configured to direct the notification circuit to generate a field loss indicator when the magnetic field sensor indicated that the magnetic field has terminated, the field loss indicator having a notification output different relative to the detection of the magnetic field.

5. The device of claim 1, wherein the notification circuit is configured to provide at least one of an auditory or vibratory notification indicating that a magnetic field is present and has a strength that exceeds a field strength threshold.

6. The device of claim 1, wherein the notification represents a stimulus with first and second unique patterns that differentiate between activation and de-activation of the magnetic field.

7. The device of claim 1, wherein the electronics circuit includes a microcontroller and the magnetic detection sensor sets a status register of the microcontroller, the microcontroller configured to confirm a magnet placement when the status register is set for a stable field duration.

8. The device of claim 1, wherein the electronics circuit is configured to deliver a tachyarrhythmia therapy and to suspend the delivery of the tachyarrhythmia therapy in response to detection of the magnetic field by the magnetic detection sensor.

9. The device of claim 1, wherein the magnetic detection sensor includes at least one of a Hall Effect sensor, a giant magnetoresistance sensor, or a reed switch.

10. The device of claim 1, wherein the magnetic detection sensor is configured to provide a magnetic field present (MFP) signal to the electronics circuit when the magnetic field sensor experiences the stable placement of the external magnetic source proximate to the implantable medical device.

11. The device of claim 1, wherein the magnetic detection sensor is configured to provide a magnetic field present (MFP) signal to the electronics circuit when the magnetic detection sensor detects a movement of a magnetic field of the external magnetic source proximate to the implantable medical device.

12. The device of claim 1, wherein the field stability criteria include strength and duration criteria that correspond to a field strength of between 1 and 10 Gauss, and a duration between 1-10 seconds.

* * * * *